United States Patent [19]

Gates

[11] 4,049,420
[45] Sept. 20, 1977

[54] CERTAIN SULFONIC ACID ESTERS OF CERTAIN 2,3-DIHYDRO-2-HYDROCARBONOXY-BENZOFURAN-5-OLS AND THEIR USE AS HERBICIDES AND PLANT GROWTH CONTROLLERS

[75] Inventor: Peter Stuart Gates, Cambridge, England

[73] Assignee: Fisons Limited, London, England

[21] Appl. No.: 579,726

[22] Filed: May 21, 1975

[30] Foreign Application Priority Data

May 31, 1974 United Kingdom .............. 24350/74

[51] Int. Cl.$^2$ ..................... A01N 9/28; C07D 307/83
[52] U.S. Cl. ................................... 71/88; 260/346.22
[58] Field of Search ...................... 260/346.2 R; 71/88

[56] References Cited

U.S. PATENT DOCUMENTS 3,689,507  9/1972  Gates et al. ................. 260/346.2 R

FOREIGN PATENT DOCUMENTS 1,271,659  4/1972  United Kingdom

*Primary Examiner*—Henry R. Jiles
*Assistant Examiner*—Bernard Dentz
*Attorney, Agent, or Firm*—Wenderoth, Lind & Ponack

[57] ABSTRACT

Compounds of formula

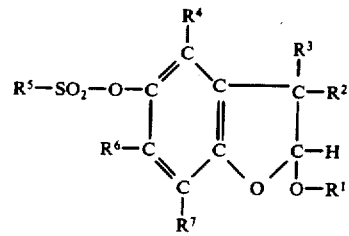

(II)

wherein $R^1$ represents a branched chain alkyl group of at least 4 carbon atoms or a cycloalkyl group of at least 4 carbon atoms;

$R^2$ and $R^3$ are the same or different and each represents a hydrogen atom or an alkyl group of 1–6 carbon atoms;

$R^4$, $R^6$ and $R^7$ are the same or different and each represent a hydrogen or halogen atom or an alkyl or alkoxy group of 1–4 carbon atoms; and $R^5$ represents an alkyl group, a substituted alkyl group, an aryl group or a substituted aryl group, are outstanding herbicides and plant growth regulants.

23 Claims, No Drawings

CERTAIN SULFONIC ACID ESTERS OF CERTAIN 2,3-DIHYDRO-2-HYDROCARBONOXY-BENZOFURAN-5-OLS AND THEIR USE AS HERBICIDES AND PLANT GROWTH CONTROLLERS

This invention relates to new compounds, their preparation, their plant use and plant physiologically active compositions containing them.

United Kingdom specification No. 1,271,659 discloses 5-benzofuranyl esters of formula:

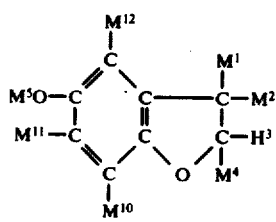

(I)

wherein $M^1$, $M^2$ and $M^3$ are the same or different and are hydrogen or alkyl, or $M^1$ and $M^2$ together or $M^2$ and $M^3$ together form an alkylene chain; where $M^4$ is hydroxy, alkoxy, substituted alkoxy, alkenyloxy, alkylthio, substituted alkenyloxy, alkynyloxy, substituted alkynyloxy, aryloxy, substituted aryloxy, $NM^6M^7$ in which $M^6$ and $M^7$ are alkyl or substituted alkyl or together with the nitrogen atom form an optionally substituted heterocyclic ring, —$OCOM^{13}$, —$OSO_2M^{14}$ or —O—O—$M^{15}$, in which $M^{13}$ is alkyl, alkenyl, alkynyl or aryl, substituted or unsubstituted, alkylamino, dialkylamino, alkoxy, aryloxy, arylamino, substituted arylamino, substituted alkoxy, substituted aryloxy, alkenyloxy, substituted alkenyloxy, alkynyloxy or substituted alkynyloxy, in which $M^{14}$ is alkyl, substituted alkyl, aryl or substituted aryl, and $M^{15}$ is alkyl, alkenyl or alkynyl; or where $M^3$ and $M^4$ together represent an oxygen atom or the group =$NM^{16}$, in which $M^{16}$ is alkyl or cycloalkyl; where $M^5$ is the group $M^8CO$—, $M^9SO_2$— or $M^9SO$—, in which $M^8$ is halogen substituted alkyl, and $M^9$ is alkyl, substituted alkyl, aryl or substituted aryl; and where $M^{10}$, $M^{11}$ and $M^{12}$ are the same or different and are hydrogen, alkyl, halogen, cyano, acyl or alkoxy. It discloses that these esters possess physiological activity, particularly, plant physiological activity, and may be used as herbicides and as plant growth regulants. Best known of these esters is 2,3-dihydro-3,3-dimethyl-2-ethoxybenzofuran-5-yl methanesulphonate, which is known particularly as a selective herbicide for use in sugar beet. A surprising group of related compounds has now been discovered.

Accordingly, the invention provides a compound of formula:

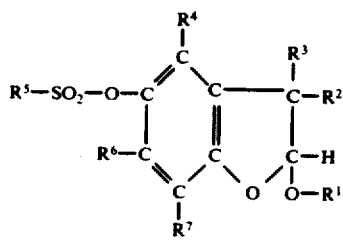

(II)

wherein $R^1$ represents a branched chain alkyl group of at least 4 carbon atoms (usually 4-10 carbon atoms, e.g. 2,2-dimethylpropyl, 1,3-dimethylbutyl, 3-methylbutyl or 2-methylpropyl) or a cycloalkyl group of at least 4 carbon atoms (usually 4-8 carbon atoms, e.g. cyclopentyl, cyclohexyl or cycloheptyl);

$R^2$ and $R^3$ are the same or different and each represent a hydrogen atom or an alkyl group of 1-6 carbon atoms (for example methyl or ethyl);

$R^4$, $R^6$ and $R^7$ are the same or different and each represent a hydrogen or halogen atom (for example chlorine or bromine) or an alkyl or alkoxy group of 1-4 carbon atoms (for example methyl, ethyl, isopropyl or methoxy); and $R^5$ represents an alkyl group (for example of 1-6 carbon atoms such as methyl or ethyl), a substituted alkyl group (for example the alkyl group substituted by halogen or alkoxy of 1-6 carbon atoms such as chloromethyl, 3-chloropropyl or methoxypropyl), an aryl group (for example phenyl) or a substituted aryl group (for example the aryl group substituted by halogen or alkyl of 1-4 carbon atoms such as chlorophenyl or tolyl).

The invention provides also a process for preparing the compound, which process comprises reacting the corresponding 5-hydroxybenzofuran of formula:

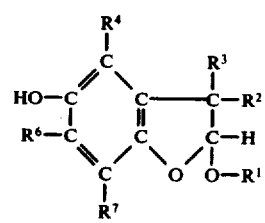

(III)

wherein $R^1$, $R^2$, $R^3$, $R^4$, $R^6$ and $R^7$ are as defined above, with an acylating agent of formula $R^5SO_xX$ wherein $R^5$ is as defined above and X represents a halogen, particularly chlorine, atom.

The invention also provides a process for preparing the compound which process comprises reacting the corresponding benzofuran of formula:

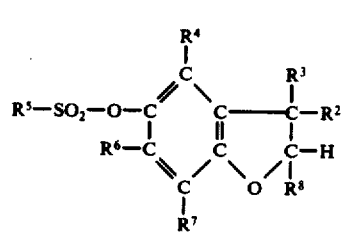

(IV)

wherein $R^2$, $R^3$, $R^4$, $R^5$, $R^6$ and $R^7$ are as defined above and $R^8$ represents a halogen, particularly chlorine, atom, or a hydroxy group, with an alcohol of formula $R^1OH$ wherein $R^1$ is as defined above. This is the preferred process.

The invention also provides a method of combating weeds at a locus infested or liable to be infested by them, which method comprises applying to the locus a weed-combating amount of the compound.

The invention provides in addition a method of regulating the growth of a plant, which method comprises applying to the locus at which the plane is growing or is to grow a plant growth regulant amount of the compound.

In addition, the invention provides a plant physiologically active composition containing the compound, especially a plant physiologically active composition comprising the compound together with at least one material selected from carriers, surface active agents, other pesticides and other plant growth regulants.

The present compounds are of surprisingly different activity spectrum on plants compared to the closely related esters such as 2,3-dihydro-3,3-dimethyl-2-ethoxybenzofuran-5-yl methanesulphonate and the compounds show unexpectedly useful selective herbicidal action. The present compounds are much less active than such esters on cereal crops such as wheat, barley and maize but have a high activity against wild oats and other weeds. The present compounds are thus surprisingly useful for the control of wild oats and other weeds in cereal crops.

In the present compounds any halogen (i.e., chlorine, bromine, fluorine or iodine) is, for convenience in manufacture, preferably chlorine. The substituted alkyl or aryl group which $R^5$ can represent is for example a monosubstituted alkyl or aryl group.

In a preferred embodiment:

$R^1$ represents an alkyl group 4-9 carbon atoms which is branched on at least one of the 1- and 2-position carbon atoms, or a cycloalkyl group of 5-7 carbon atoms;

$R^2$ and $R^3$ each represent methyl;

$R^4$, $R^6$ and $R^7$ each represent a hydrogen atom; and $R^5$ represents an alkyl group of 1-3 carbon atoms optionally substituted by halogen.

When $R^1$ represents a cycloalkyl group of at least 4 carbon atoms, it is preferably cyclohexyl. It is preferred, however, that $R^1$ represents a branched chain alkyl group of at least 4 carbon atoms, e.g. 4-9 carbon atoms, and especially of 4-6 carbon atoms. In a preferred embodiment, at least one of the 1-, 2- and 3-position carbon atoms is branched, e.g. when $R^1$ represents 2,2-dimethylpropyl or 1,4-dimethylpentyl.

$R^1$ preferably represents 1,3-dimethylbutyl or 2-methylpropyl, especially the latter.

$R^2$ and $R^3$ preferably represent the same or different alkyl groups of 1-6 carbon atoms, for example each can represent methyl.

$R^4$, $R^6$ and $R^7$ preferably each represent a hydrogen atom.

$R^5$ preferably represents an alkyl group, particularly methyl.

The following are particularly outstanding:

2,3-dihydro-3,3-dimethyl-2-(2,2-dimethylpropoxy)-benzofuran-5-yl methanesulphonate;

2,3-dihydro-3,3-dimethyl-2-(1,3-dimethylbutoxy)benzofuran-5-yl methanesulphonate;

2,3-dihydro-3,3-dimethyl-2-(3-methylbutoxy)benzofuran-5-yl methanesulphonate;

2,3-dihydro-3,3-dimethyl-2-(2-methylpropoxy)benzofuran-5-yl methanesulphonate; and 2,3-dihydro-3,3-dimethyl-2-(cyclohexyloxy)benzofuran-5-yl methanesulphonate; especially the second and fourth compounds named.

2,3-Dihydro-3,3-dimethyl-2-(2-methylpropoxy)benzofuran-5-yl methanesulphonate is particularly preferred.

The production of the present compounds is usually conducted by reaction in an inert solvent, though this is not essential.

The reaction with an acylating agent of formula $R^5SO_2X$ is preferably carried out in the presence of an acid acceptor such as an organic base (for example triethylamine or pyridine) or an inorganic base (for example sodium carbonate or bicarbonate).

The reaction of the benzofuran of formula IV with an alcohol of formula $R^1OH$ is preferably conducted with heating. Preferred ways of conducting the reaction are:

a. heating the 2-hydroxy compound with the alcohol of formula $R^1OH$ (e.g. in the presence of an acid catalyst) and eliminating water formed, e.g. by distilling the reactants in a solvent such as benzene, for example under reflux using one equivalent of the alcohol $R^1OH$ and a Dean and Stark trap and carrying out the reaction until one equivalent of water has been eliminated;

b. heating the 2-hydroxy compound, e.g. under reflux, with excess, preferably a large excess, of the alcohol $R^1OH$, in the presence of an acid catalyst; and c. heating the 2-chloro compound, e.g. under reflux, with excess, preferably a large excess, of the alcohol $R^1OH$.

The benzofuran starting materials are either known or can be prepared by ways known in themselves. The benzofuran starting materials of formula IV in which $R^8$ represents a chlorine, bromine or iodine atom may be prepared by replacing the 2-hydroxy group of the corresponding 2-hydroxy compound by a chlorine, bromine or iodine atom, e.g. by reacting the 2-hydroxy compound with thionyl chloride. The benzofuran starting materials of formula IV in which $R^8$ represents a fluorine, bromine or iodine atom may be prepared by reacting the corresponding compound in which $R^4$ represents a chlorine atom with a metal fluoride, bromide or iodide respectively.

The present compounds are active on plant physiology, affecting the growth of plants so that the compounds may be used as herbicides or plant growth regulants. The plant physiologically active compositions can be prepared by admixing the ingredients. Usually the compositions are initially produced in the form of concentrates, e.g. containing 0.5-85% of the present compound, and these are diluted with water or hydrocarbon, usually water, for application, generally such that the concentration of the compound is 0.05-5%. Percentages and parts in this specification are by weight unless otherwise indicated.

The compositions normally contain a surface active agent and/or a carrier.

The composition may be liquid and contain a liquid carrier, e.g. water (e.g. water used to dilute a concentrate for application). If water is employed as carrier in a concentrate, an organic solvent may also be present as carrier, though this is not usually employed. A surface active agent may advantageously be present.

The liquid carrier may be other than water, for example an organic solvent, usually a water-immiscible solvent, e.g. a hydrocarbon which boils within the range 130°-270° C, in which the compound is dissolved or suspended. A concentrate containing an organic solvent suitably also contains a surface active agent so that the concentrate acts as a self-emulsifiable oil on admixture with water.

The composition may be solid and contain a solid carrier which may be finely divided. Examples of suitable solids are clays, sand, mica, chalk, attapulgite, diatomite, perlite and sepiolite, and synthetic solid carriers, e.g. silicas, silicates and lignosulphonates.

Wettable powders soluble or dispersable in water may be formed by admixing the compound with or without a solid carrier with a surface active agent.

The term 'surface active agent' is used in the broad sense to include materials variously called emulsifying agents, dispersing agents and wetting agents. Such agents are well known in the art.

The surface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic agents, for example cetyl trimethylammonium bromide.

Preferred surface active agents include fatty alkyl sulphates, alkyl aryl sulphonates, fatty alkyl ethoxylates, sulphated fatty alkyl ethoxylates, dialkyl sulphosuccinate esters, lignin sulphonate salts, sulphonated naphthalene-formaldehyde condensates and sulphonated urea-formaldehyde condensates.

The present active compound may be admixed with another pesticide, e.g. herbicide, insecticide or fungicide, or with another plant growth regulant or with a fertilizer. Particular advantages are obtained with mixtures with a second herbicide. The present compound may be used sequentially with a second herbicide, e.g. one herbicide applied before planting or before emergence of a crop and the other herbicide applied after emergence of the crop.

The second herbicide may be for example a phenoxyaliphatic acid, substituted urea, triazine, phenol, nitrile, bipyridylium compound, substituted benzoic acid, halogenated aliphatic acid, carbamate, thiocarbamate, chloroacetamide, diazine or arsenic herbicide. In respect of selective herbicidal compositions for post-emergence use, the second herbicide may be for example a substituted phenoxyaliphatic acid; in respect of selective herbicidal compositions for pre-emergence use, the second herbicide may be for example a substituted urea or triazine; in respect of sequential use, the present compound may for example be applied pre-emergence and 4-chloro-2-butynyl N-(3-chlorophenyl) carbamate post-emergence.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples of the substituted phenoxyaliphatic acids which may be mentioned include 2,4-dichlorophenoxyacetic acid, 2-methyl-4-chloro-phenoxyacetic acid; 2,4,5-trichlorophenoxyacetic acid, gamma-2,4-dichlorophenoxybutyric acid, gamma-2-methyl-4-chlorophenoxybutyric acid and alpha-2-methyl-4-chlorophenoxypropionic acid.

The substituted urea generally comprises a tri- or tetra-substituted urea such as N'-parachlorophenyl-N,N-dimethylurea, N-butyl-N'-(3,4-dichlorophenyl)-N-methylurea, N'-parachlorophenyl-O,N,N-trimethylisourea, N'-p-chlorophenyl-N-methoxy-N-methylurea and N,N-dimethyl-N'-phenylurea.

The triazine herbicide generally comprises a compound of the formula:

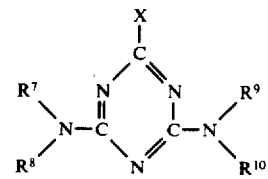

where X is a halogen, OY group or SY group, where Y is an alkyl group, and $R^7$, $R^8$, $R^9$ and $R^{10}$ are hydrogen or alkyl, such as 2-chloro-4,6-bisethylamino-1,3,5-triazine or 2-chloro-6-ethylamino-4-isopropylamino-1,3,5-triazine.

The phenol herbicide generally comprises 4,6-dinitro-o-cresol or pentachlorophenol. The nitrile herbicide generally comprises 3,5-diiodo-4-hydroxybenzonitrile, 3,5-dibromo-4-hydroxybenzonitrile or 2,6-dichlorobenzonitrile. The bipyridylium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichlorobenzoic acid or 2-methoxy-3,6-dichlorobenzoic acid. The halogenated aliphatic acid herbicide generally comprises trichloroacetic acid or 2,2-dichloropropionic acid. The carbamate herbicide generally comprises 3-methoxycarbonylaminophenyl m-tolylcarbamate, 3-ethoxycarbonylaminophenyl N-phenylcarbanate, 3-methoxycarbonylaminophenyl N-(3,5-dimethylphenyl)-carbamate, isopropyl N-(3-chlorophenyl) carbamate or 4-chloro-2-butynyl N-(3-chlorophenyl) carbamate. The thiocarbamate herbicide generally comprises S-ethyl N,N-dipropylthiocarbamate, S-ethyl N,N-diisobutylthiocarbamate, S-(2,3,3-trichloroallyl)-N,N-diisopropylthiocarbamate or S-(2,3-dichloroallyl) N,N-diisopropylthiocarbamate. The chloroacetamide herbicide generally comprises N,N-diallyl-2-chloroacetamide or N-isopropyl-2-chloroacetanilide. The diazine herbicide generally comprises 5-bromo-6-methyl-3secbutyluracil, 3-cyclohexyl-5,6-trimethyleneuracil, 5-amino-4-chloro-2-phenyl-3-pyridazinone or 1,2-dihydropyridazine-3,6-dione. The arsenic herbicide generally comprises a salt of methane arsonic acid or cacodylic acid. Other herbicides which may be used in such mixtures include aminotriazole, 2,3-dichloro-1,4-naphthoquinone, 4-amino-3,5,6-trichloropicolinic acid, 2,6-dinitro-N,N-dipropyl-4-trifluoromethylaniline, and S,S,S-tributyl phosphorotrithioate.

The ratio of the present compound to the second herbicide may vary over a wide range according to the particular compounds involved and the intended use. In general the ratio of present compound to second herbicide lies in the range 1:0.1 to 1:15.

The present compounds may be in admixture with a non-phytotoxic oil, e.g. Agri-Oil Plus or Sun Oil 11E.

In the use of the present compounds as total herbicides, high rates of application, for example at least 10 kg per hectare, such as 10–25 kg per hectare, of the compounds are usually required, unless they are mixed with other active components, in which case the rate can be reduced.

In the use of the present compounds as selective herbicides, the rate of application is usually much lower and may be for example 0.5-8 kg per hectare, such as 1-4 kg per hectare.

In the use of the compounds as plant growth regulants, low rates of application are usually required such as 0.1-4, e.g. 0.5-1, kg per hectare.

The present compounds can be applied to plants, the soil, land or aquatic areas. They are outstandingly useful as herbicides, particularly selective herbicides, especially for selectively combating weeds by application to a locus at which a crop, e.g. a food crop (for example sugar beet, potatoes, peas, beans and particularly a cereal crop such as wheat, barley or maize) or other crops (for example sunflowers), is growing or is to grow. They may be applied pre- or, preferably, post-planting of the crop. They may be applied post- or, preferably, pre-emergence of the crop. They are particularly useful for pre-emergent selective weed control in wheat or barley The invention is illustrated by the following Examples.

EXAMPLE 1

A mixture of 2,3-dihydro-3,3-dimethyl-2-hydroxybenzofuran-5-yl methanesulphonate (13g, 0.05 mole), 3-methyl-1-butanol (4.4g, 0.05 mole) and concentrated sulphuric acid (4 drops) in benzene (50 ml) was heated at reflux under a Dean and Stark trap until 0.9 ml water (0.05 mole) had been eliminated. The reaction mixture was cooled, washed with dilute aqueous sodium hydroxide solution and with water (twice) and dried over sodium sulphate. The benzene was then distilled off under reduced pressure to give 2,3-dihydro-3,3-dimethyl-2-(3-methylbutoxy)-5-benzofuranyl methanesulphonate as a yellow oil (14 g, 86% yield) which slowly solidified (melting point 35°–38° C).

Analysis Found: C, 58.40; H, 7.70; S, 9.95%. $C_{16}H_{24}O_5S$ requires: C, 58.51; H, 7.37; S, 9.76%.

EXAMPLE 2

A solution of 2,3-dihydro-3,3-dimethyl-2-hydroxybenzofuran-5-yl methanesulphonate (13g, 0.05 mole) in isobutand (50 ml) to which was added concentrated sulphuric acid (6 drops) was boiled under reflux for three hours. The solution was then cooled, taken into ether (250 ml), washed with dilute aqueous sodium hydroxide solution and with water (twice) and dried over sodium sulphate. The solvent was then distilled off under reduced pressure to give 2,3-dihydro-3,3-dimethyl-2-(2-methylpropoxy) benzofuran-5-yl methanesulphonate (15g, 96% yield) as a white solid, melting point 84°–86° C.

Analysis Found: C, 57.35; H, 6.80%. $C_{15}H_{22}O_5S$ requires: C, 57.30; H, 7.05%.

EXAMPLE 3

A solution of 2-chloro-2,3-dihydro-3,3-dimethylbenzofuran-5-yl methanesulphonate (14g, 0.05 mole) in 1,1-dimethylpropanol (50 ml) was boiled under reflux for 4½ hours. After cooling, the solution was taken into ether (250 ml), washed with dilute aqueous sodium hydroxide solution (twice) and with water (twice) and dried over sodium sulphate. The solvent was then distilled off under reduced pressure to give 2,3-dihydro-3,3-dimethyl-2-(1,1-dimethylpropoxy)benzofuran-5-yl methanesulphonate (7g, 43% yield) as a pale yellow oil.

Analysis Found: C, 58.00; H, 7.00; S, 9.70%. $C_{16}H_{24}O_5S$ requires: C, 58.51; H, 7.37; S, 9.76%.

EXAMPLES 4–48

The following table lists compounds of general formula II in which $R^2$ and $R^3$ each represent methyl and $R^4$, $R^6$ and $R^7$ each represent hydrogen which were prepared by a process analogous to that of Example 1, 2 or 3. In each case, satisfactory elemental analysis was obtained. Where no melting point is given in the table, the compounds were liquid at room temperature.

| Example | $R^1$ | $R^5$ | Example to which analogous | m.p. |
|---|---|---|---|---|
| 4 | sec-butyl | methyl | 2 | — |
| 5 | tert-butyl | methyl | 3 | — |
| 6 | 1-methylbutyl | methyl | 1 | — |
| 7 | 1-ethylpropyl | methyl | 1 | — |
| 8 | 2-methylbutyl | methyl | 1 | — |
| 9 | 1,2-dimethylpropyl | methyl | 1 | — |
| 10 | 2,2-dimethylpropyl | methyl | 1 | — |
| 11 | 1-methylpentyl | methyl | 1 | — |
| 12 | 1-ethylbutyl | methyl | 1 | — |
| 13 | 2,2-dimethylbutyl | methyl | 1 | — |
| 14 | 1,2,2-trimethylpropyl | methyl | 1 | — |
| 15 | 2-ethylbutyl | methyl | 1 | — |
| 16 | 1-ethyl-2-methylpropyl | methyl | 1 | — |
| 17 | 1,3-dimethylbutyl | methyl | 1 | 40–44° |
| 18 | 2-methylpentyl | methyl | 1 | — |
| 19 | 1-methylhexyl | methyl | 1 | — |
| 20 | 1-ethylpentyl | methyl | 1 | — |
| 21 | 1-propylbutyl | methyl | 1 | — |
| 22 | 2,2-dimethylpentyl | methyl | 1 | 55–57° |
| 23 | 1-isopropyl-2-methylpropyl | methyl | 3 | 70–73° |
| 24 | 1-isopropylbutyl | methyl | 1 | 34–36° |
| 25 | 1-ethyl-3-methylbutyl | methyl | 1 | — |
| 26 | 1-ethyl-2-methylbutyl | methyl | 1 | — |
| 27 | 1,2-dimethylpentyl | methyl | 3 | — |
| 28 | 1,4-dimethylpentyl | methyl | 1 | — |
| 29 | 1-methylheptyl | methyl | 1 | — |
| 30 | 1-ethylhexyl | methyl | 1 | — |
| 31 | 2-ethyl-4-methylpentyl | methyl | 1 | — |
| 32 | 2,2,4-trimethylpentyl | methyl | 1 | 76–78° |
| 33 | 2-ethylhexyl | methyl | 1 | — |
| 34 | 1,5-dimethylhexyl | methyl | 1 | — |
| 35 | 1-methyloctyl | methyl | 1 | — |

-continued

| Example | R¹ | R⁵ | Example to which analogous | m.p. |
|---|---|---|---|---|
| 36 | 1-propylhexyl | methyl | 1 | — |
| 37 | 1-isobutyl-3-methylbutyl | methyl | 1 | — |
| 38 | cyclopentyl | methyl | 1 | — |
| 39 | cyclohexyl | methyl | 1 | — |
| 40 | cycloheptyl | methyl | 1 | — |
| 41 | 2-methylpropyl | ethyl | 1 | — |
| 42 | 2,2-dimethylpropyl | ethyl | 1 | — |
| 43 | 1,3-dimethylbutyl | ethyl | 1 | — |
| 44 | 2-methylpropyl | propyl | 1 | — |
| 45 | 2,2-dimethylpropyl | propyl | 1 | — |
| 46 | 1,3-dimethylbutyl | propyl | 1 | — |
| 47 | 2-methylpropyl | 3-chloropropyl | 1 | — |
| 48 | 2,2-dimethylpropyl | 3-chloropropyl | 1 | — |

EXAMPLES 49-52

The compounds listed below were each formulated as attaclay/sand dusts and incorporated into John Innes No. 1 potting compost at a rate of 26 parts per million weight/volume of active ingredient to soil (equivalent to a soil surface application of approximately 11.2 kilogrammes of compound per hectare cultivated to a depth of 5 cm). The treated soil was placed in anodised aluminum pans, 20 cm long × 10 cm wide × 5 cm deep. Seeds of peas (*Pisum sativum*), mustard (*Sinapis alba*), linseed (*Linum usitatissimum*), maize (*Zea mays*), oats (*Avena sativa*) and ryegrass (*Lolium sp*) were sown in the treated soil, one species per pan, watered and placed in a controlled environment room, (temperature 22° C, relative humidity 65-85%, artifical illumination 14 hours per day at 13000 lux) for 21 days. The plants were then visually assessed for any herbicidal effect, all differences from untreated controls being scored on a scale from 0 to 100 in which 0 signifies no effect and 100 signifies complete suppression of growth. The results are summarised in the following table:

| Compound | Peas | Mustard | Linseed | Maize | Oats | Ryegrass |
|---|---|---|---|---|---|---|
| 2,3-Dihydro-3,3-dimethyl-2-(2,2-dimethylpropoxy)-benzofuran-5-yl methanesulphonate | 5 | 0 | 0 | 4 | 95 | 0 |
| 2,3-Dihydro-3,3-dimethyl-2-(1,3-dimethylbutoxy) benzofuran-5-yl methanesulphonate | 10 | 3 | 5 | 5 | 94 | 0 |
| 2,3-Dihydro-3,3-dimethyl-2-(3-methylbutoxy)benzofuran-5-yl methanesulphonate | 15 | 20 | 3 | 5 | 93 | 2 |
| 2,3-Dihydro-3,3-dimethyl-2-(2-methylpropoxy) benzofuran-5-yl methanesulphonate | 30 | 50 | 30 | 15 | 94 | 20 |

EXAMPLE 53

A wettable powder formulation was obtained from the following:

| | |
|---|---|
| 2,3-dihydro-3,3-dimethyl-2-(2-methylpropoxy)-benzofuran-5-yl methanesulphonate | 20% |
| 'Reax 45L' (combined wetting and dispersing agent based on lignin sulphonate) | 20% |
| China clay | 6% |
| | 74% |

EXAMPLE 54

An emulsifiable concentrate formulation was obtained from the following:

| | |
|---|---|
| 2,3-dihydro-3,3-dimethyl-2-(1,3-dimethylbutoxy) benzofuran-5-yl methanesulphonate | 250g |
| 'Arylan Ca' (calcium dodecylbenzenesulphonate) | 25g |
| 'Ethylan C40 AH' (condensation product of castor oil with 40 moles of ethylene oxide) | 25g |
| Solvent 200 (aromatic hydrocarbon comprising mixed methyl naphthalenes) | to 1 liter |

EXAMPLE 55

The formulation of Example 53 was admixed with water and sprayed in field trials in England at a rate of 4 kg of the 2,3-dihydro-3,3-dimethyl-2-(2-methylpropoxy)benzofuran-5-yl methanesulphonate per hectare pre-emergence on to various plant species listed in the table below. In comparison, 2,3-dihydro-3,3-dimeth-yl-2-ethoxybenzofuran-5-yl methanesulphonate was sprayed at half that rate at the same time on to similar plots. After 9 weeks, the herbicidal activity of the compounds was assessed visually as a percentage effect. Results are shown below, each result being the mean of two replicates.

| | The 2-methyl-propoxy compound, 4 kg/ha | The 2-ethoxy compound, 2 kg/ha |
|---|---|---|
| Maize (*Zea mays*) | 5 | 15 |
| Barley (*Hordeum vulgare*) | 0 | 45 |
| Onion (*Allium cepa*) | 35 | 32 |
| Carrot (*Daucus carota*) | 20 | 20 |
| Potato (*Solanum tuberosum*) | 0 | 30 |
| Peas (*Pisum sativum*) | 0 | 10 |

-continued

| | The 2-methyl-propoxy compound, 4 kg/ha | The 2-ethoxy compound, 2 kg/ha |
|---|---|---|
| Sunflower (*Helianthus annus*) | 0 | 10 |

The safety on these crops of the present compound compared to a closely related one is apparent.

EXAMPLE 56

The formulation of Example 54 was admixed with water and sprayed in field trials in England at a rate of 4 kg of the 2,3-dihydro-3,3-dimethyl-2-(1,3-dimethylbutoxy)benzofuran-5-yl methanesulphonate per hectare on to various plant species at the stage of post-emergence shown in the table below. In comparison, 2,3-dihydro-3,3-dimethyl-2-ethoxybenzofuran-5-yl methanesulphonate was sprayed at half that rate at the same time on to similar plots. 4 weeks later, the herbicidal activity of the compounds was assessed visually as a percentage effect. Results are shown below, each result being the mean of two replicates.

| | Growth stage at time of application | The 2-dimethylbutoxy compound, 4 kg/ha | The 2-ethoxy compound, 2 kg/ha |
|---|---|---|---|
| Maize (*Zea mays*) | 6 leaves | 15 | 60 |
| Barley (*Hordeum vulgare*) | tillering | 0 | 38 |
| Mustard (*Sinapis alba*) | 5 nodes (coming into flower) | 5 | 10 |
| Carrot (*Daucus carota*) | 1 pair of true leaves | 17 | 25 |
| Potato (*Solanum tuberosum*) | approximately 12 cm in height | 30 | 75 |
| Peas (*Pisum sativum*) | 5 nodes | 0 | 15 |
| French beans (*Phaseolus vulgaris*) | 2 pairs of true leaves | 10 | 10 |
| Sunflower (*Helianthus annuus*) | 2 pairs of true leaves | 49 | 72 |

The safety on these crops of the present compound compared to a closely related one is apparent.

EXAMPLES 57 and 58

The formulations of Examples 53 and 54 were admixed with water and sprayed in greenhouse trials in England at the rates of active ingredient shown in the table pre-emergence on to wheat, barley and wild oats. The percentage herbicidal effect is shown.

| | Rate, kg/ha | Wheat | Barley | Wild oats |
|---|---|---|---|---|
| Example 57 The 2-methylpropoxy compound | 4.0 | 10 | 0 | 80 |
| Example 58 The 2-dimethylbutoxy compound | 16.0 | 0 | 0 | 90 |
| | 8.0 | 0 | 0 | 80 |
| | 4.0 | 0 | 0 | 60 |
| | 2.0 | 0 | 0 | 45 |

The safety to wheat and barley and the activity against wild oats is apparent.

EXAMPLES 59 and 60

The formulations of Examples 53 and 54 were admixed with water and sprayed in greenhouse trials in England at the rates of active ingredients shown in the table below post-emergence on to wheat, barley, blackgrass and wild oats. The percentage herbicidal effect is shown.

| | Rate, kg/ha | Wheat | Barley | Black grass | Wild oats |
|---|---|---|---|---|---|
| Example 59 The 2-methylpropoxy compound | 8.0 | 0 | 0 | 0 | 45 |
| Example 60 The 2-dimethylbutoxy compound | 16.0 | 0 | 15 | 65 | 70 |
| | 8.0 | 0 | 0 | 0 | 45 |

The safety to wheat and barley and activity against wild oats and blackgrass (the 2-dimethylbutoxy compound) is apparent.

I claim:
1. A compound of the formula

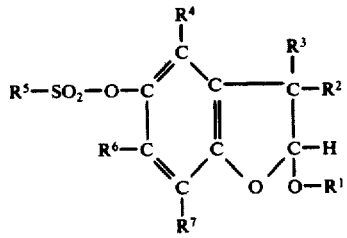

wherein $R^1$ represents a branched chain alkyl group of 4 to 10 carbon atoms wherein at least the 2-position is branched or cyclohexyl, $R^2$ and $R^3$ are the same or different and each represents a hydrogen atom or an alkyl group of 1 - 6 carbon atoms, $R^4$, $R^6$ and $R^7$ are the same or different and each represents a hydrogen or halogen atom or an alkyl or alkoxy group of 1 - 4 carbon atoms, and $R^5$ represents an alkyl group of 1 - 6 carbon atoms, an alkyl group of 1 - 6 carbon atoms substituted by halogen or alkoxy of 1 - 6 carbon atoms, phenyl, or phenyl substituted by halogen or alkyl of 1 - 4 carbon atoms.

2. A compound according to claim 1 wherein $R^5$ represents an alkyl group of 1 - 6 carbon atoms, an alkyl group of 1 - 6 carbon atoms monosubstituted by halogen or alkoxy of 1 - 6 carbon atoms, phenyl or phenyl monosubstituted by halogen or alkyl or 1 - 4 carbon atoms.

3. A compound according to claim 1 wherein $R^5$ represents an alkyl group of 1 - 6 carbon atoms.

4. A compound according to claim 1, wherein the branched chain alkyl group of $R^1$ is additionally branched at the 1- or 3-position.

5. A compound according to claim 1 wherein the branched chain alkyl group of $R^1$ is additionally branched at the 1- and 3-positions.

6. A compound according to claim 1 wherein the $R^1$ branched chain alkyl group is of 4 to 6 carbon atoms.

7. A compound according to claim 1 wherein $R^2$ and $R^3$ represent the same or different alkyl groups of 1 to 6 carbon atoms.

8. A compound according to claim 1 wherein $R^4$, $R^6$ and $R^7$ each represent a hydrogen atom.

9. A compound according to claim 1 wherein $R^1$ is a branched chain alkyl group of 4 to 9 carbon atoms, wherein at least the 2-position is branched or cyclohexyl, $R^2$ and $R^3$ each are methyl, $R^4$, $R^6$ and $R^7$ each is hydrogen, and $R^5$ is alkyl of 1 - 3 carbon atoms or halo alkyl of 1 to 3 carbon atoms .

10. A compound according to claim 1 which is 2,3-dihydro-3,3-dimethyl-2-(2,2-dimethylpropoxy)benzofuran-5-yl methanesulphonate.

11. A compound according to claim 1 which is 2,3-dihydro-3,3-dimethyl-2-(2-methylpropoxy)benzofuran-5-yl methanesulphonate.

12. A compound according to claim 1 which is 2,3-dihydro-3,3-dimethyl-2-(cyclohexyloxy)benzofuran-5-yl methanesulphonate.

13. A plant growth control composition which comprises an effective amount of a compound according to claim 1 in admixture with at least one member selected from the group consisting of an inert carrier therefor and a surface active agent, said composition being suitable for application to plants or to the locus at which plants are growing or are to grow.

14. A composition according to claim 13 which contains a surface active agent.

15. A solid composition according to claim 13 wherein said carrier is a solid.

16. A liquid composition according to claim 13 wherein the carrier is a liquid hydrocarbon which boils within the range of 130° to 270° C.

17. A herbicidal composition which comprises a herbicidally effective amount of a compound according to claim 1 in admixture with an inert carrier therefor.

18. A method for combatting weeds at a locus infested or liable to be infested by them, which method comprises applying to the locus a weed-combatting amount of a compound according to claim 1.

19. A method for controlling the growth of plants, which method comprises applying to the locus at which the plants are growing or are to grow, a plant growth controlling amount of a compound according to claim 1.

20. A method according to claim 18 wherein weeds are selectively combatted by applying the compound to a locus at which a crop is growing or is to grow.

21. A method according to claim 18 wherein weeds are selectively combatted by applying the compound to a locus at which a food crop is growing.

22. A method according to claim 20 wherein the crop is a cereal crop.

23. A method according to claim 18 wherein 0.5 to 8 kg of the compound is applied per hectare.

* * * * *